(12) United States Patent
Castellano et al.

(10) Patent No.: US 6,755,220 B2
(45) Date of Patent: Jun. 29, 2004

(54) METHOD AND APPARATUS FOR FILLING OR REFILLING A NEEDLE-LESS INJECTOR

(75) Inventors: Thomas P. Castellano, Santa Monica, CA (US); Roger R. Wise, Chatsworth, CA (US); Seth D. Levy, Los Angeles, CA (US)

(73) Assignee: Penjet Corporation, Santa Monica, CA (US)

( * ) Notice: Subject to any disclaimer, the term of this patent is extended or adjusted under 35 U.S.C. 154(b) by 0 days.

(21) Appl. No.: 10/134,511

(22) Filed: Apr. 25, 2002

(65) Prior Publication Data

US 2002/0161334 A1 Oct. 31, 2002

Related U.S. Application Data

(60) Provisional application No. 60/286,875, filed on Apr. 27, 2001.

(51) Int. Cl.[7] .................................................. B65B 3/04
(52) U.S. Cl. ........................ 141/27; 141/25; 141/383; 604/68
(58) Field of Search ..................... 141/2, 18, 21, 141/25–27, 383; 604/68–72

(56) References Cited

U.S. PATENT DOCUMENTS

| | | |
|---|---|---|
| 1,997,129 A | 4/1935 | Taylor et al. |
| 2,221,739 A | 11/1940 | Reiter |
| 2,605,763 A | 8/1952 | Smoot |
| 2,632,445 A | 3/1953 | Kas, Sr. |
| 2,642,062 A | 6/1953 | May |
| 2,680,439 A | 6/1954 | Sutermeister |
| 2,695,023 A | 11/1954 | Brown |
| 2,718,299 A | 9/1955 | Atwater et al. |
| 2,754,818 A | 7/1956 | Scherer |
| 3,110,310 A | 11/1963 | Cislak |
| 3,131,692 A | 5/1964 | Love |
| 3,141,583 A | 7/1964 | Mapel et al. |
| 3,293,749 A | 12/1966 | George et al. |
| 3,348,545 A | 10/1967 | Sarnoff et al. |
| 3,481,510 A | 12/1969 | Allen |
| 3,507,276 A | 4/1970 | Burgess |
| 3,517,668 A | 6/1970 | Brickson |
| 3,557,784 A | 1/1971 | Shields |
| 3,583,399 A | 6/1971 | Ritsky |
| 3,688,765 A | 9/1972 | Gasaway |
| 3,695,266 A | 10/1972 | Lussier |
| 3,853,125 A | 12/1974 | Clark et al. |
| 3,859,996 A | 1/1975 | Mizzy et al. |

(List continued on next page.)

FOREIGN PATENT DOCUMENTS

| | | |
|---|---|---|
| CA | 1103314 | 2/1978 |
| CA | 1258 019 | 8/1989 |
| CH | 293302 | 9/1953 |
| DE | 22140 | 4/1883 |
| DE | 730971 | 1/1943 |
| DE | 1070 784 | 6/1960 |
| EP | 0143 895 | 8/1984 |
| EP | 0220 146 | 4/1987 |
| EP | 0295 917 | 6/1988 |

(List continued on next page.)

Primary Examiner—J. Casimer Jacyna
(74) Attorney, Agent, or Firm—Pillsbury Winthrop LLP

(57) ABSTRACT

Devices and methods are described for filling or refilling a needle-less injector. A coupling device is attached to a vessel, and mated to the dispensing end of a needle-less injector. A volume of fluid may be transferred via the coupling device, from the vessel to the injector. Air may be removed from the injector prior to the injector, vessel, and coupling device being separated from one another. In alternate embodiments, the vessel may include filling equipment capable of filling or refilling multiple needle-less injectors simultaneously, in series, or both. In other embodiments, a coupling device may be used to withdraw a fluid from a storage vial into a vessel for filling a needle-less injector. A storage vial may alternately contain a product, and a fluid may be introduced therein via a coupling device to create a mixture, which may be subsequently withdrawn into a vessel for filling a needle-less injector.

94 Claims, 9 Drawing Sheets

U.S. PATENT DOCUMENTS

| | | |
|---|---|---|
| 3,894,663 A | 7/1975 | Carhart et al. |
| 3,946,732 A | 3/1976 | Hurscham |
| 3,977,574 A | 8/1976 | Thomas |
| 4,022,207 A | 5/1977 | Citrin |
| 4,031,892 A | 6/1977 | Hurschman |
| 4,033,378 A | 7/1977 | Pauliukonis |
| 4,099,548 A | 7/1978 | Sturm et al. |
| 4,114,619 A | 9/1978 | Wagner |
| 4,139,008 A | 2/1979 | Wagner |
| 4,146,029 A | 3/1979 | Ellinwood, Jr. |
| 4,169,474 A | 10/1979 | Wagner |
| 4,284,077 A | 8/1981 | Wagner |
| 4,333,458 A | 6/1982 | Margulies et al. |
| 4,338,980 A | 7/1982 | Schwebel et al. |
| 4,393,870 A | 7/1983 | Wagner |
| 4,395,921 A | 8/1983 | Oppenlander |
| 4,413,760 A | 11/1983 | Paton |
| 4,415,101 A | 11/1983 | Shapiro et al. |
| 4,425,121 A | 1/1984 | Young et al. |
| 4,435,173 A | 3/1984 | Siposs et al. |
| 4,444,560 A | 4/1984 | Jacklich |
| 4,457,712 A | 7/1984 | Dragan |
| 4,470,317 A | 9/1984 | Sabloewski et al. |
| 4,475,905 A | 10/1984 | Himmelstrup |
| 4,498,904 A | 2/1985 | Turner et al. |
| 4,526,294 A | 7/1985 | Hirschmann et al. |
| 4,529,401 A | 7/1985 | Leslie et al. |
| 4,538,616 A | 9/1985 | Rogoff |
| 4,573,970 A | 3/1986 | Wagner |
| 4,581,022 A | 4/1986 | Leonard et al. |
| 4,592,745 A | 6/1986 | Rex et al. |
| 4,596,556 A | 6/1986 | Morrow et al. |
| 4,600,403 A | 7/1986 | Wagner |
| 4,613,328 A | 9/1986 | Boyd |
| 4,659,327 A | 4/1987 | Bennett et al. |
| 4,664,128 A | 5/1987 | Lee |
| 4,676,781 A | 6/1987 | Phillips et al. |
| 4,680,027 A | 7/1987 | Parsons et al. |
| 4,710,172 A | 12/1987 | Jacklich et al. |
| 4,710,178 A | 12/1987 | Leonard et al. |
| 4,722,728 A | 2/1988 | Dixon |
| 4,743,229 A | 5/1988 | Chu |
| 4,790,824 A | 12/1988 | Morrow et al. |
| 4,820,287 A | 4/1989 | Leonard |
| 4,834,149 A | 5/1989 | Fournier et al. |
| 4,865,591 A | 9/1989 | Sams |
| 4,874,367 A | 10/1989 | Edwards |
| 4,883,472 A | 11/1989 | Michel |
| 4,913,699 A | 4/1990 | Parsons |
| 4,936,833 A | 6/1990 | Sams |
| 4,941,880 A | 7/1990 | Burns |
| 4,950,246 A | 8/1990 | Muller |
| 4,959,056 A | 9/1990 | Dombrowski et al. |
| 4,998,570 A | 3/1991 | Strong |
| 5,009,634 A | 4/1991 | Feldman et al. |
| 5,009,637 A | 4/1991 | Newman et al. |
| 5,024,656 A | 6/1991 | Gasaway et al. |
| 5,050,612 A | 9/1991 | Matsumura |
| 5,064,413 A | 11/1991 | McKinnon et al. |
| 5,069,668 A | 12/1991 | Boydman |
| 5,074,044 A | 12/1991 | Smith et al. |
| 5,085,642 A | 2/1992 | Sarnoff et al. |
| 5,088,996 A | 2/1992 | Kopfer et al. |
| 5,092,842 A | 3/1992 | Bechtold et al. |
| 5,102,393 A | 4/1992 | Sarnoff et al. |
| 5,104,380 A | 4/1992 | Holman et al. |
| 5,112,317 A | 5/1992 | Michel |
| 5,114,406 A | 5/1992 | Gabriel et al. |
| 5,139,484 A | 8/1992 | Hazon et al. |
| 5,180,371 A | 1/1993 | Spinello |
| 5,226,895 A | 7/1993 | Harris |
| 5,226,896 A | 7/1993 | Harris |
| 5,244,461 A | 9/1993 | Derlien |
| 5,244,465 A | 9/1993 | Michel |
| 5,249,584 A | 10/1993 | Karkar et al. |
| 5,254,100 A | 10/1993 | Huband |
| 5,256,157 A | 10/1993 | Samiotes et al. |
| 5,267,977 A | 12/1993 | Feeney, Jr. |
| 5,279,294 A | 1/1994 | Anderson et al. |
| 5,279,584 A | 1/1994 | Dillard, III et al. |
| 5,279,585 A | 1/1994 | Balkwill |
| 5,279,586 A | 1/1994 | Balkwill |
| 5,330,430 A | 7/1994 | Sullivan |
| 5,342,309 A | 8/1994 | Hausser |
| 5,354,287 A | 10/1994 | Wacks |
| 5,383,865 A | 1/1995 | Michel |
| 5,425,716 A | 6/1995 | Kawasaki et al. |
| 5,429,602 A | 7/1995 | Hauser |
| 5,445,620 A | 8/1995 | Haber et al. |
| 5,480,381 A | 1/1996 | Weston |
| 5,499,972 A | 3/1996 | Parsons |
| 5,503,627 A | 4/1996 | McKinnon et al. |
| 5,509,905 A | 4/1996 | Michel |
| 5,520,639 A | 5/1996 | Peterson et al. |
| 5,536,249 A | 7/1996 | Castellano et al. |
| 5,540,664 A | 7/1996 | Wyrick |
| 5,569,189 A | 10/1996 | Parsons |
| 5,593,388 A | 1/1997 | Phillips |
| 5,593,390 A | 1/1997 | Castellano et al. |
| 5,630,796 A | 5/1997 | Bellhouse et al. |
| 5,649,912 A | 7/1997 | Peterson |
| 5,704,911 A | 1/1998 | Parsons |
| 5,713,873 A | 2/1998 | Jehle |
| 5,728,074 A | 3/1998 | Castellano et al. |
| 5,730,723 A | 3/1998 | Castellano et al. |
| 5,746,714 A | 5/1998 | Salo et al. |
| 5,820,602 A | 10/1998 | Kovelman et al. |
| 5,851,198 A | 12/1998 | Castellano et al. |
| 5,891,085 A | 4/1999 | Lilley et al. |
| 5,891,086 A | 4/1999 | Weston |
| 5,891,092 A | 4/1999 | Castellano |
| 5,893,397 A | 4/1999 | Peterson et al. |
| 5,899,880 A | 5/1999 | Bellhouse et al. |
| 5,925,021 A | 7/1999 | Castellano et al. |
| 5,957,166 A | 9/1999 | Safabash |
| 5,957,886 A | 9/1999 | Weston |
| 5,993,412 A | 11/1999 | Deily et al. |
| 6,063,053 A | 5/2000 | Castellano et al. |
| 6,080,130 A | 6/2000 | Castellano |
| 6,096,002 A | 8/2000 | Landau |
| 6,132,395 A | 10/2000 | Landau et al. |
| 6,135,979 A | 10/2000 | Weston |
| D434,323 S | 11/2000 | Pattison |
| 6,145,762 A | 11/2000 | Orloff et al. |
| 6,149,625 A | 11/2000 | Weston et al. |
| 6,156,008 A | 12/2000 | Castellano |
| 6,168,587 B1 | 1/2001 | Bellhouse et al. |
| 6,174,304 B1 | 1/2001 | Weston |
| 6,223,786 B1 | 5/2001 | Castellano |
| 6,302,160 B2 | 10/2001 | Castellano |
| 6,309,371 B1 | 10/2001 | Deboer et al. |
| 6,406,455 B1 | 6/2002 | Willis et al. |

FOREIGN PATENT DOCUMENTS

| | | |
|---|---|---|
| EP | 0347 190 | 6/1989 |
| EP | 0368 191 | 11/1989 |
| EP | 0416 975 | 8/1990 |
| EP | 0427 457 | 11/1990 |
| FR | 1170 312 | 1/1959 |
| FR | 1378829 | 11/1964 |
| FR | 78 05814 | 3/1978 |

| | | | | | |
|---|---|---|---|---|---|
| FR | 2557 445 | 12/1984 | WO | 92/13583 | 2/1992 |
| FR | 2 749169 | 6/1996 | WO | 95/03844 | 7/1994 |
| GB | 1225495 | 6/1967 | WO | 9529720 | 11/1995 |
| GB | 1574 267 | 2/1978 | WO | 96/19252 | 12/1995 |
| GB | 2109 690 | 2/1982 | WO | 96/28202 | 3/1996 |
| WO | 0037 696 | 3/1981 | WO | 97/13537 | 10/1996 |
| WO | 85/02546 | 10/1984 | WO | 97/25015 | 1/1997 |
| WO | 08/08469 | 3/1989 | WO | 48654 | 8/2000 |

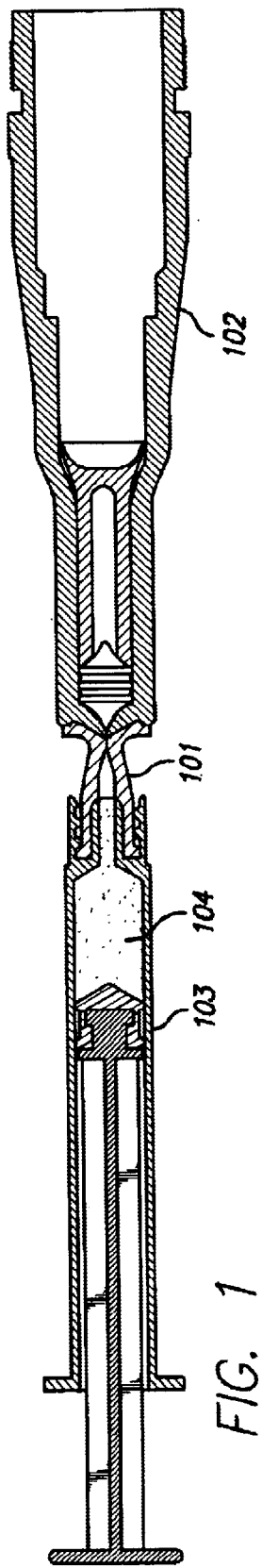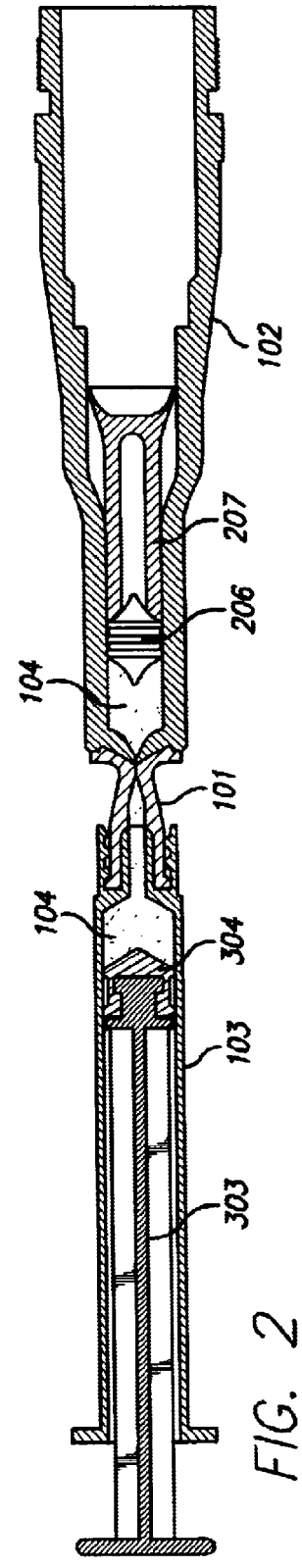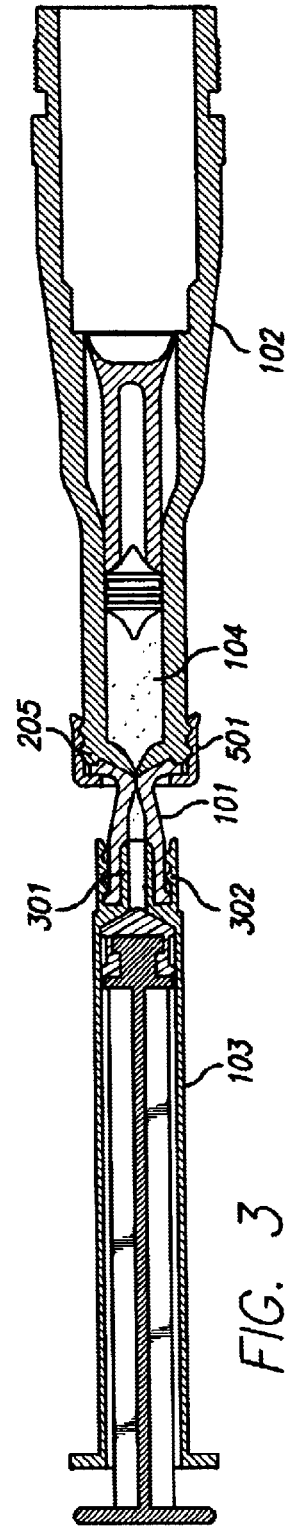

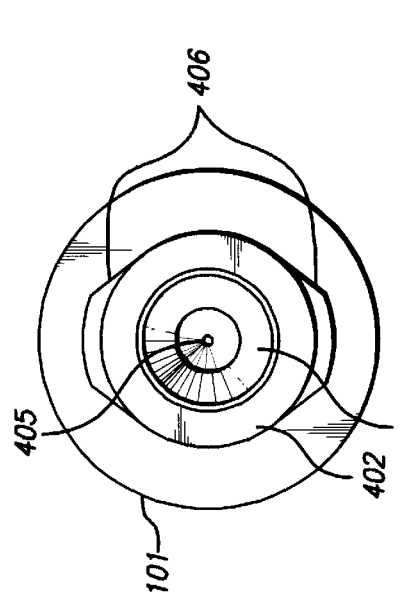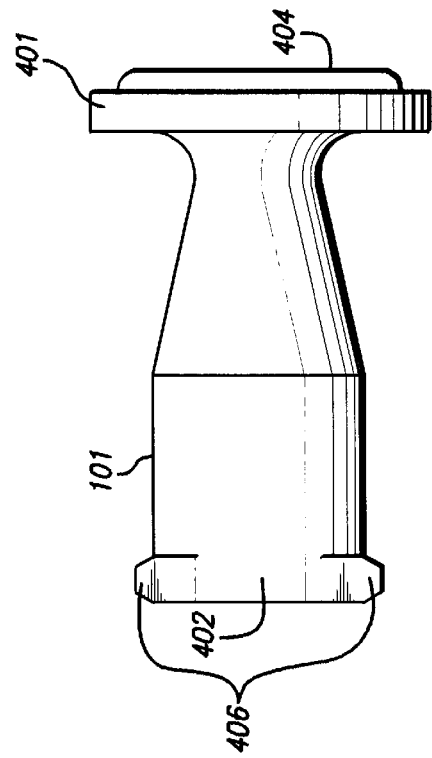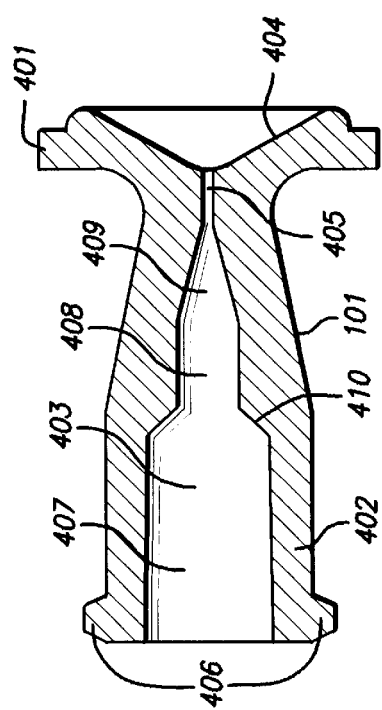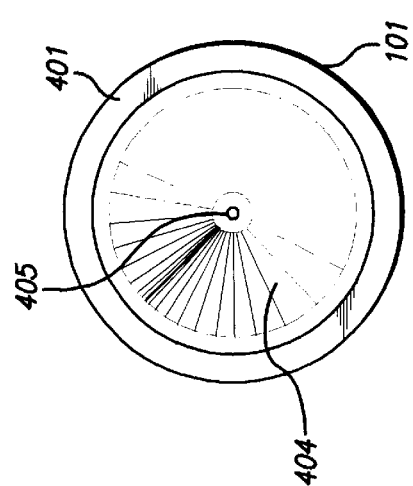

ary conventions.

METHOD AND APPARATUS FOR FILLING OR REFILLING A NEEDLE-LESS INJECTOR

RELATED APPLICATIONS

This application claims the benefit of priority under 35 U.S.C. §119 of U.S. provisional patent application serial No. 60/286,875, filed Apr. 27, 2001, the contents of which are hereby incorporated by reference in their entirety.

This application is related to U.S. patent application Ser. No. 10/011,534, filed Oct. 26, 2001, now U.S. Pat. No. 6,673,034, which is a divisional of U.S. patent application Ser. No. 09/566,928, filed May 6, 2000, now U.S. Pat. No. 6,447,475, and U.S. patent application Ser. No. 09/834,476, filed Apr. 13, 2001, now U.S. Pat. No. 6,613,010. This application is also related to U.S. patent application Ser. No. 09/433,916, filed Nov. 3, 1999, now U.S. Pat. No. 6,302,160, which is a continuation-in-part of U.S. patent application Ser. No. 09/192,145, filed Nov. 14, 1998, now U.S. Pat. No. 6,223,786, and to U.S. patent application Ser. No. 10/034,561, filed Dec. 26, 2001, now U.S. Pat. No. 6,474,369.

Further, this application generally relates to U.S. patent application Ser. No. 09/215,769, filed Dec. 19, 1998, now U.S. Pat. No. 6,063,053, which is a continuation of U.S. patent application Ser. No. 08/727,911, filed Oct. 9, 1996, now U.S. Pat. No. 5,851,198, which is a continuation-in-part of U.S. patent application Ser. No. 08/719,459, filed Sep. 25, 1996, now U.S. Pat. No. 5,730,723, which is a continuation-in-part of U.S. patent application Ser. No. 08/541,470, filed Oct. 10, 1995, now abandoned. This application is also generally related to U.S. patent application Ser. No. 09/192,079, filed Nov. 14, 1998, now U.S. Pat. No. 6,080,130, to U.S. patent application Ser. No. 09/808,511, filed Mar. 14, 2001, now U.S. Pat. No. 6,500,239, and to U.S. patent application Ser. No. 10/086,374, filed Oct. 22, 2001.

FIELD OF THE INVENTION

This invention relates to the filling of needle-less injectors, and, in particular embodiments, to devices and methods for filling or refilling modular gas-pressured needle-less injectors.

BACKGROUND OF THE INVENTION

Traditionally, fluids such as medications are injected into patients, either subdermally or intradermally, using hypodermic syringe needles. The body of the syringe is filled with the injectable fluid and, once the needle has pierced the patient's skin, the syringe plunger is depressed so as to expel the injectable fluid out of an opening in the needle. The person performing the injection is often a trained medical services provider, who manually inserts the hypodermic needle between the layers of a patient's skin for an intradermal injection, or beneath the skin layers for a subcutaneous injection. However, injections are also routinely performed by laypersons, as in the case of diabetics self-administering insulin injections.

Needle injectors suffer from increased danger of contamination exposure to health care workers administering injections, and to the general public when such injectors are not properly disposed of In fact, safety considerations surrounding needle injectors are of such paramount concern that they are prohibited from some locations. This may severely hamper the ability of those in need of regular injections to receive convenient and timely medical attention. One heavily burdened population is diabetic children who require insulin injections, since children are not permitted to bring needle injectors to some school campuses. Various hospitals are similarly working to minimize the use of needles; some going so far as to design and mandate a completely needle-free environment.

Jet injectors are generally configured to avoid some or all of these problems inherent in needle-containing injectors. Typically, needle-less medication injectors use either an expansion spring or a compressed inert gas to propel the fluid medication (via a push rod plunger) through a small orifice (an injector nozzle) which rests perpendicular to and against the injection site. The fluid medication is generally accelerated at a high rate to a speed of between about 800 feet per second (fps) and 1,200 fps (approximately 244 and 366 meters per second, respectively). This causes the fluid to pierce through the skin surface without the use of a needle, resulting in the medication being deposited in a flower pattern under the skin surface.

U.S. Pat. No. 6,447,475, U.S. Pat. No. 6,080,130, U.S. Pat. No. 6,063,053, U.S. Pat. No. 5,851,198, U.S. Pat. No. 5,730,723, and U.S. patent application Ser. No. 09/834,476, now U.S. Pat. No. 6,613,010, each of which is incorporated by reference in its entirety, describe needle-less injectors incorporating a gas power source, thus obviating some of the limitations inherent in compression spring injectors and addressing many of the concerns of conventional jet injectors. The injectors described therein have a pre-filled and self-contained compressed gas for providing pressure to inject medication into the skin surface of a patient without the use of a needle.

Some injectors may be furnished to a hospital or consumer in a pre-filled state (i.e., the needle-less injector already contains a volume of the fluid sought to be injected). Filling such a device a substantial amount of time prior to use presents a variety of concerns, not the least of which is the risk of bacterial contamination on the exterior of such a device owing to fluid remaining on the exterior thereof after the filling operation is completed.

Additionally, as some ailments require periodic injection of varying amounts of a medication, it may be impractical for a user to employ a pre-filled needle-less injector. By design, a pre-filled injector already contains a particular amount of a medication, and in the case of an injection whose requisite volume cannot be determined in advance, one can not assume that the volume of a pre-filled injector will be suitable. Also, if multiple injections are to be administered throughout the day, one may not wish to carry several pre-filled injectors, as this may be cumbersome and inconvenient.

Finally, various medications or other products suited for use in conjunction with a needle-less injector are provided in either a solid or binary form. Solid medications may be lyophilized, for example, wherein a component of the final injectate is in a freeze-dried or similar form. The lyophilized component may be mixed with a liquid shortly before injecting the resulting solution by needle-less injection. Binary medications may include, for example, two liquids that are mixed together shortly before injection of the resulting mixture. U.S. Pat. No. 6,223,786, U.S. Pat. No. 6,302,160, and U.S. patent application Ser. No. 10/034,561 describe various methods and devices for performing this type of mixing and also filling needle-less injectors with such a mixture, and each is incorporated by reference in its entirety.

SUMMARY OF THE DISCLOSURE

It is therefore an object of an embodiment of the instant invention to provide an apparatus and method that obviates, for practical purposes, the above-mentioned limitations.

In one embodiment of the instant invention, a coupling device is provided. The coupling device may connect the dispensing end of a needle-less injector to a vessel containing a fluid. In various embodiments, the vessel may be a Luer syringe, filling equipment configured to fill a needle-less injector, or another appropriate apparatus. The coupling device may be contoured such that, when it is mated to a needle-less injector and fluid is transferred therethrough, the fluid does not contact the exterior surface of the dispensing end of the needle-less injector. The coupling device may also include a fitting for removably affixing the device to a needle-less injector at one end, and may further include an attachment mechanism for removably affixing the device to an appropriate vessel at the opposing end. In preferred embodiments, graduations on either the vessel, the injector, or both provide a user with visual cues regarding filling, so that the user can determine when a desirable volume of fluid has been filled into the injector.

In another embodiment of the instant invention, a filling device is provided. The filling device may mate to the dispensing end of a needle-less injector, and may include a coupling device and a vessel. In various embodiments, the vessel may be a Luer syringe or other apparatus configured to fill a needle-less injector. The coupling device may be contoured such that, when the filling device is mated to a needle-less injector and fluid is transferred therefrom, the fluid does not contact the exterior surface of the dispensing end of the needle-less injector. The filling device may also include a fitting for removably affixing the device to a needle-less injector at one end, and may further include an attachment mechanism for affixing the coupling device to the vessel. In preferred embodiments, graduations on either the vessel, the injector, or both provide a user with visual cues regarding filling, so that the user can determine when a desirable volume of fluid has been filled into the injector.

In still another embodiment of the instant invention, a method is provided for filling a needle-less injector. The method may include providing a coupling device configured to be simultaneously mated to a needle-less injector and attached to a vessel, and to provide fluid communication therebetween. An appropriate vessel and needle-less injector may be mated to the coupling device, and fluid may then be expelled from the vessel, through the coupling device, and into the needle-less injector. Graduations may be included on the vessel, the injector, or both; graduations allowing a user to ascertain the volume of fluid that has been transferred. Filling may be terminated upon reaching a predetermined volume, as indicated by observing the graduations (i.e., in those embodiments wherein graduations are included). The direction of flow may be reversed after expelling a desired volume of fluid from the vessel to remove gas bubbles from the injector. Finally, the vessel, the coupling device, and the injector may be disconnected from one another.

In yet another embodiment of the instant invention, a storage vial adapted for use with a coupling device is provided. The storage vial may be contoured, such that, when it is mated to a coupling device, a fluid transferred between the storage vial and the coupling device does not contact the exterior surface of the storage vial. The storage vial may contain a product that is in solid or liquid form. A product in liquid form, such as a fluid, may be drawn from the storage vial through the coupling device and into a vessel configured on the opposite end of the coupling device. Alternatively, a fluid may be introduced into the storage vial, wherein it may mix with a liquid or solid (e.g., lyophilized) product already contained therein. The resulting mixture may then be drawn from the storage vial through the coupling device and into a vessel configured on the opposite end of the coupling device. The vessel may then be used in accordance with the methods described above with respect to alternative embodiments of the present invention to fill a needle-less injector.

BRIEF DESCRIPTION OF THE DRAWINGS

FIG. 1 illustrates a cross-sectional view of a coupling device in accordance with an embodiment of the instant invention. The coupling device is simultaneously attached to a vessel and mated to a needle-less injector. A fluid is included in the vessel and the needle-less injector is void of fluid.

FIG. 2 illustrates a cross-sectional view of a coupling device in accordance with an embodiment of the instant invention. The coupling device is simultaneously attached to a vessel and mated to a needle-less injector. A fluid is partially transferred from the vessel into the needle-less injector, such that both the vessel and the needle-less injector contain an amount of the fluid.

FIG. 3 illustrates a cross-sectional view of a coupling device in accordance with an embodiment of the instant invention. The coupling device is simultaneously attached to a vessel and mated to a needle-less injector. A fluid is included in the needle-less injector and the vessel is void of fluid.

FIGS. 4a–d illustrate a coupling device in accordance with an embodiment of the instant invention. FIG. 4a is a side cross-sectional view thereof; FIG. 4b is a perspective view from a vessel end thereof; FIG. 4c is a perspective view from an injector end thereof; and FIG. 4d is a side perspective view thereof FIG. 5a is a side cross-sectional view thereof; FIG. 5b is a perspective view from an injector end thereof; FIG. 5c is a perspective view from a vessel end thereof; and FIG. 5d is a side perspective view thereof FIG. 6a is a side cross-sectional view thereof; FIG. 6b is a perspective view from an exterior end thereof; FIG. 6c is a perspective view from an injector end thereof; and FIG. 6d is a side perspective view thereof

FIG. 8a depicts the coupling device mated to the needle-less injector, and FIG. 8b depicts the coupling device mated to the needle-less injector with an injector attachment mechanism.

FIG. 10 illustrates a coupling device in accordance with an embodiment of the instant invention. The coupling device is attached to filling equipment.

FIG. 12a depicts a coupling device attached to a vessel containing a fluid and to a storage vial containing a product. FIG. 12b depicts the introduction of the fluid into the storage vial from the vessel, and the subsequent creation of a mixture in the storage vial. FIG. 12c depicts the storage vial being inverted such that it is positioned above the vessel and coupling device. FIG. 12d depicts the removal of mixture from the storage vial into the vessel.

DETAILED DESCRIPTION

Figure 5A:
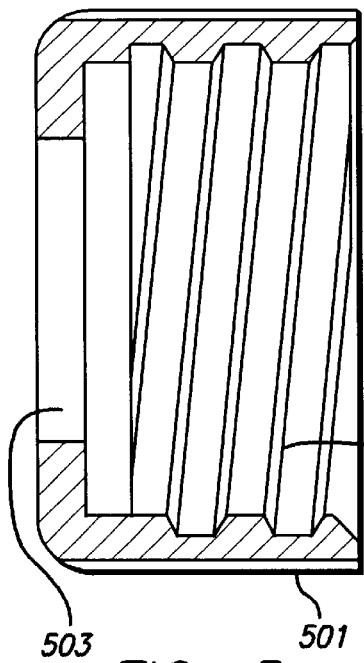
FIGS. 5a–d illustrate an injector attachment mechanism in accordance with an embodiment of the instant invention.

As shown in the drawings for purposes of illustration, an aspect of the invention is embodied in a coupling device. The coupling device may be used to provide fluid communication between a needle-less injector and a vessel. With fluid communication established therebetween, fluid may be transferred from the vessel into the needle-less injector. A needle-less injector may be void of fluid prior to filling via the coupling device, although in alternate embodiments, the needle-less injector may contain a latent fluid (i.e., any fluid present in the needle-less injector prior to the introduction of fluid contained in the vessel), a lyophilized solid, a non-lyophilized solid, or any other suitable product. In such alternate embodiments, the coupling device allows for the introduction of a fluid into the needle-less injector, wherein it may mix with the latent fluid, the lyophilized solid, or the other product contained therein.

In an alternate embodiment, a product may be initially contained in a storage vial. As above, the product may be a latent fluid, a lyophilized solid, a non-lyophilized solid, or any other suitable product. The storage vial may be adapted to mate with the injector end of a coupling device, such that the coupling device may be utilized to provide fluid communication between the storage vial and a vessel. In this configuration, a fluid may be drawn out of the storage vial and into a vessel. The fluid may thereafter be filled into a needle-less injector by removing the storage vial and mating the coupling device to a needle-less injector. Or, in an alternate embodiment, a product may be contained in the storage vial, and fluid contained in a vessel may be introduced into the storage vial wherein the fluid and the product may mix to form a mixture. The mixture may be subsequently drawn out of the storage vial and into the vessel. The mixture may thereafter be filled into a needle-less injector by removing the storage vial and mating the coupling device to a needle-less injector. This latter embodiment may be advantageous for the storage and mixing of lyophilized products, or various products that do not have a long shelf life when stored in solution.

Fluids appropriate for use with the instant invention include, but are not limited to, proteins, vitamins, hormones, drugs, vaccines, medications, lyophilized medications, medication cocktails, reagents, diluents, water, saline solution, and any other fluid that may be used in conjunction with a needle-less injector.

For ease in describing the illustrations, as used herein, an "injector end" refers to that terminus of an element of a coupling device that is oriented in the direction of an injector or a storage vial when the coupling device is mated thereto. Also, as used herein, a "vessel end" refers to that terminus of a particular element of a coupling device that is oriented in the direction of a vessel when the coupling device is attached thereto.

The coupling device of the instant invention may be used to fill any suitable needle-less injector, as will be readily appreciated by one in the art. Any appropriate contour may be configured on the injector end of the coupling device of the present invention to provide a surface suitable for mating with the receiving surface on the dispensing end of a particular needle-less injector. However, in preferred embodiments, the needle-less injector is a modular gas-pressured needle-less injector, such as those described in U.S. Pat. No. 6,447,475, U.S. Pat. No. 6,080,130, U.S. Pat. No. 6,063,053, U.S. Pat. No. 5,851,198, U.S. Pat. No. 5,730,723, and U.S. patent application Ser. No. 09/834,476, now U.S. Pat. No. 6,613,010, each of which has been incorporated by reference, as noted above.

The coupling device and methods of the instant invention may be utilized to fill or refill needle-less injectors. As utilized herein, the term "fill" includes within its scope the term "refill," and the term "filling" includes within its scope the term "refilling." As such, any reference to "fill" or "filling" encompasses "refill" and "refilling," respectively.

Moreover, the coupling device and methods of the instant invention may be employed to fill needle-less injectors that are completely assembled, or, in alternate embodiments, needle-less injectors whose assembly is not fully complete. For example, a coupling device of the instant invention may be temporarily mated to the housing of a needle-less injector or the ampoule of a needle-less injector, while the housing or ampoule is attached only to those other elements necessary for filling to be performed (e.g., in one embodiment, a driver 206 and a piston 207, as depicted in FIGS. 1, 2, and 3). Thus, as used herein, the term "needle-less injector" encompasses fully assembled injectors, or a-combination of only those parts of an injector necessary for purposes of filling.

In one embodiment, the vessel is a Luer syringe (FIGS. 1, 2, and 3). A Luer syringe may have a dispensing end that includes screw threading configured to operably receive an attachment mechanism of another device, such as the coupling device of the instant invention. A Luer syringe may further include a plunger 303 with a head 304 (FIG. 2). However, a variety of other vessels, such as various syringes, may be used as a vessel in accordance with alternate embodiments of the present invention.

Figure 10A:
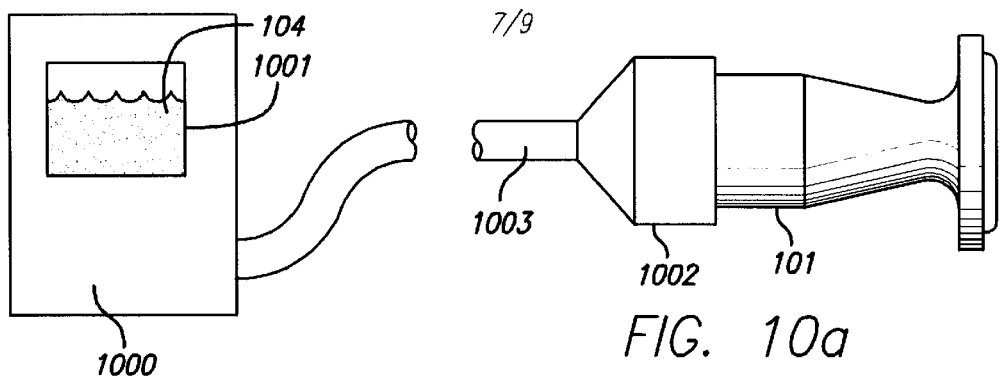
FIG. 10a depicts a single coupling device attached to filling equipment.
Figure 10B:
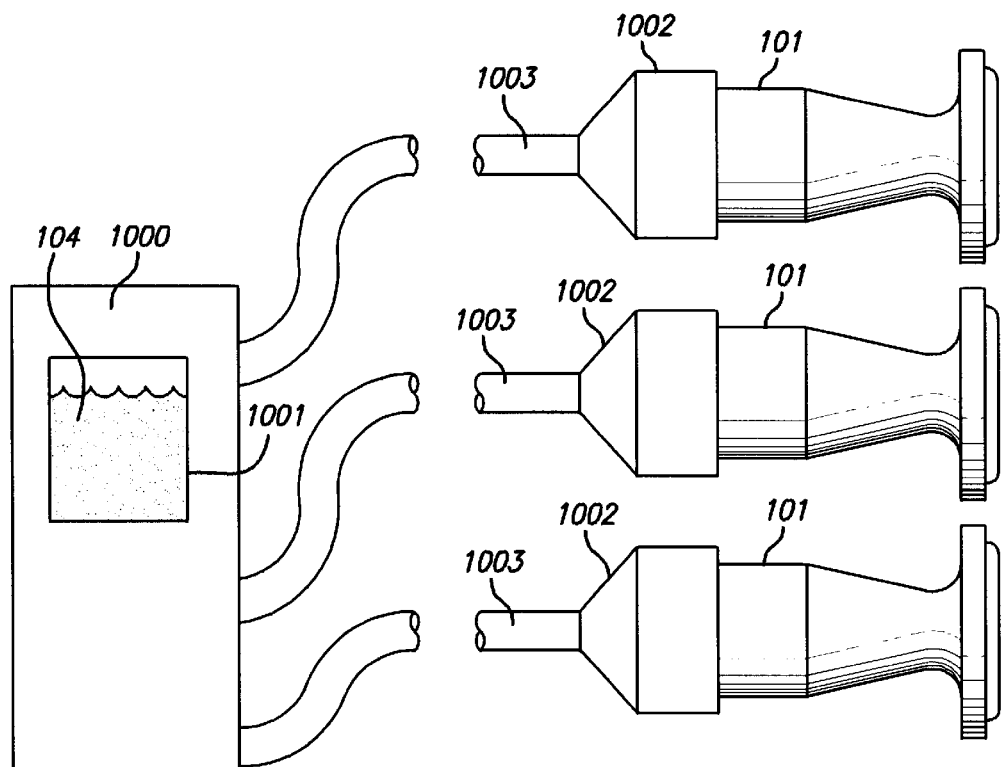
FIG. 10b depicts multiple coupling devices attached to filling equipment.

In another embodiment, the vessel may include filling equipment configured to fill at least one needle-less injector (FIG. 10). Such filling equipment may be of any appropriate assembly, and may include a variety of components suitable for performing a filling operation. For example, as depicted in FIG. 10a, such filling equipment may include a reservoir of fluid. Furthermore, as depicted in FIG. 10b, such filling equipment may be configured to fill multiple needle-less injectors. A coupling device that is attached to filling equipment may be sequentially mated to a series of needle-less injectors, introducing fluid into each. Alternatively, a number of coupling devices that are attached to filling equipment may be simultaneously mated to a group of needle-less injectors, introducing fluid into each. In yet another embodiment, however, a number of coupling devices that are attached to filling equipment may be simultaneously mated to a group of needle-less injectors, introducing fluid into each, the same coupling devices being subsequently mated to another group of needle-less injectors, introducing fluid into each, as well.

As depicted in FIG. 1, in an embodiment of the instant invention, a coupling device 101 is provided. The coupling device may be roughly cylindrical in shape to correspond to a roughly cylindrical needle-less injector 102 and/or a roughly cylindrical vessel 103. The coupling device 101 may be non-cylindrical in shape, however, especially if either the injector 102 or the vessel 103 is non-cylindrical. The coupling device 101 may be used to transfer a fluid 104 between the vessel 103 and the needle-less injector 102.

Figure 11:
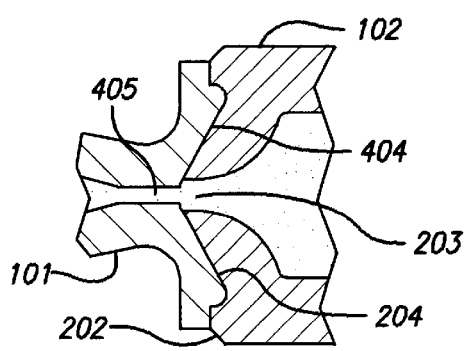
FIG. 11 illustrates the mating of a coupling device to a needle-less injector in accordance with an embodiment of the instant invention.

As depicted in FIG. 4, a coupling device 101 may include an injector end 401 (FIG. 4c) and a vessel end 402 (FIG. 4b) with a channel 403 configured therebetween. As depicted in FIGS. 4a, 4c, and 11, the coupling device 101 may include a mating surface 404, which contacts a receiving surface 204 on the dispensing end 202 of a needle-less injector 102 when the coupling device 101 and injector 102 are mated or affixed to one another. The mating surface 404 may be contoured to at least partially conform to the contour of the receiving surface 204. The mating surface 404 may further include an orifice 405, configured to align with a dispensing orifice 203 included on the receiving surface 204 of a needle-less injector 102 (FIG. 11). In the embodiment depicted in FIG. 11, the orifice 405 is positioned at the central axis of the coupling device 101, and the dispensing orifice 203 is similarly positioned at the central axis of the needle-less injector 102. The coupling device 101 may include multiple orifices (not shown) disposed in the mating surface 404, and the needle-less injector 102 may similarly include multiple dispensing orifices (not shown) disposed in the receiving surface 204 that may align therewith.

To avoid contamination or the growth of bacteria on the exterior of the dispensing end 202 of an injector 102, the exterior of the dispensing end 202 may remain free of fluid, especially fluid that might foster the growth of bacteria. Thus, in one embodiment, illustratively depicted in FIG. 11, the orifice 405 may be smaller in diameter than the dispensing orifice 203, such that fluid does not contact the receiving surface 204 or another portion of the dispensing end 202 of the injector 102 upon filling; thereby minimizing the potential for fluid being deposited on the dispensing end 202. Including an orifice 405 and a dispensing orifice 203 of similar diameters may accomplish the same goal of maintaining a fluid-free receiving surface 204.

Figure 8A:
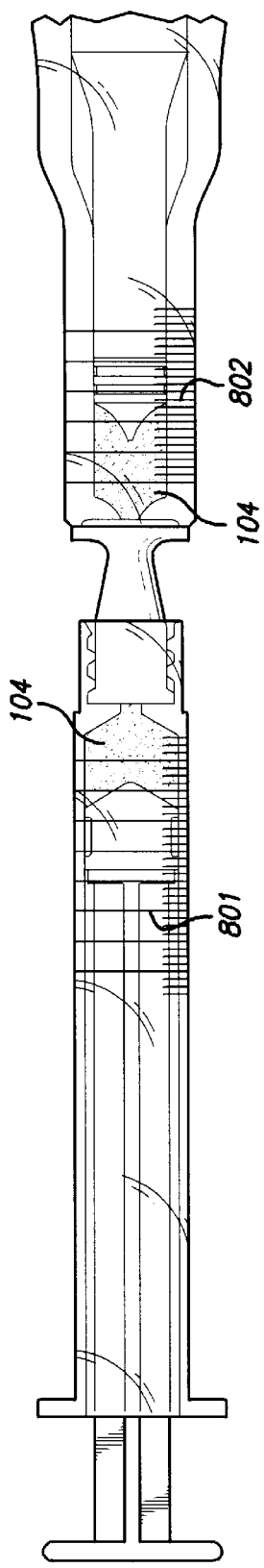
FIGS. 8a–b illustrate a side perspective view of a coupling device in accordance with an embodiment of the instant invention. The coupling device is simultaneously attached to a vessel and mated to a needle-less injector. A fluid is partially transferred from the vessel into the needle-less injector, such that both the vessel and the needle-less injector contain an amount of the fluid. Graduations are included on both the vessel and the needle-less injector.
Figure 8B:
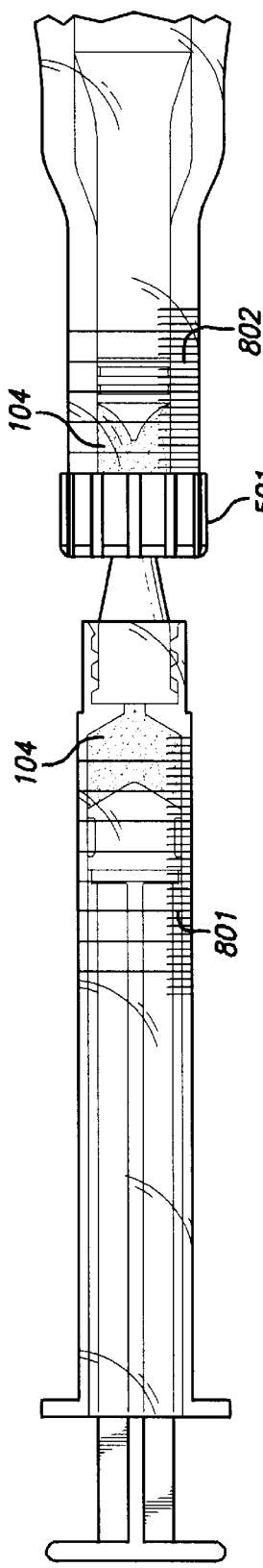

As depicted in FIG. 5a, the injector end 401 of the coupling device 101 may include an injector attachment mechanism 501 to affix the coupling device 101 to a needle-less injector 102. The injector attachment mechanism 501 may be mechanically affixed to the coupling device 101, or may remain a separate unit that a user attaches over the coupling device 101 such that the coupling device 101 remains firmly against the needle-less injector 102 during a filling thereof (FIGS. 3 and 8b). However, the injector attachment mechanism 501 is not required to fill a needle-less injector 102 with a coupling device 101; instead, in various embodiments, the coupling device 101 may be unaffixedly mated to the needle-less injector 102 (FIGS. 1, 2, and 8a).

Figure 5B:
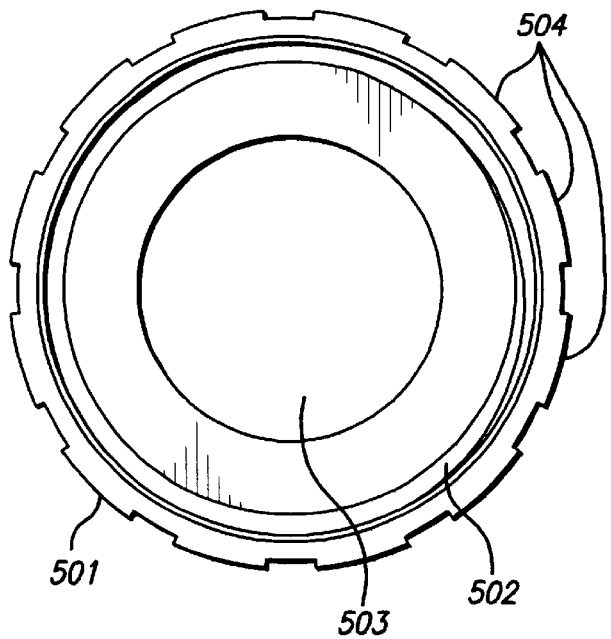

As shown in FIGS. 5a and 5b, an injector attachment mechanism 501 may include an attachment fitting 502. The attachment fitting 502 depicted in FIGS. 5a and 5b is an interior screw threading, though any other suitable attachment fitting 502 may be employed, such as a pressure fitting, a snap fitting, or the like. Correspondingly, as depicted in FIG. 3, a needle-less injector 102 may include an injector attachment receiving mechanism 205 configured to cooperate with the attachment fitting 502 of the injector attachment mechanism 501. In the embodiment illustratively depicted in FIG. 3, an injector attachment receiving mechanism 205 is embodied in an exterior screw threading that may cooperate with interior screw threading on the injector attachment mechanism 501.

Figure 5C:
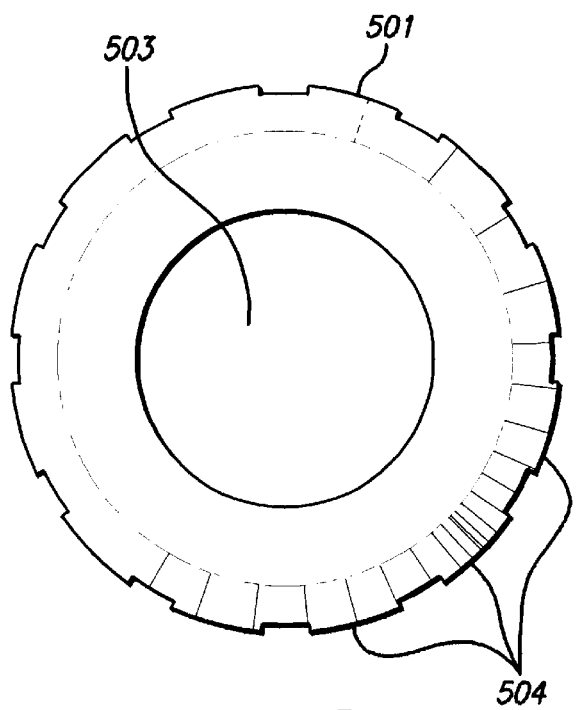
Figure 5D:
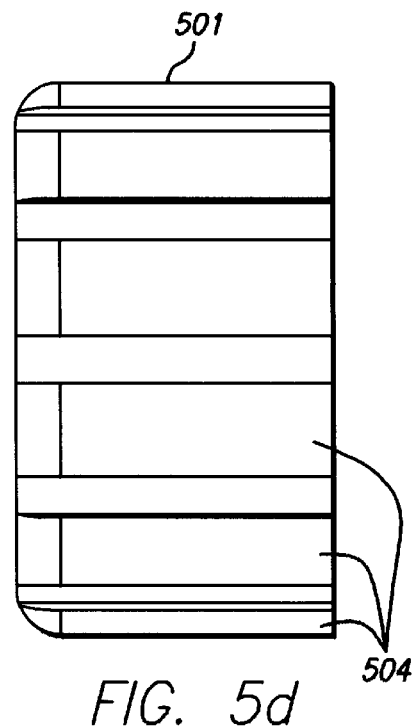
Figure 6A:
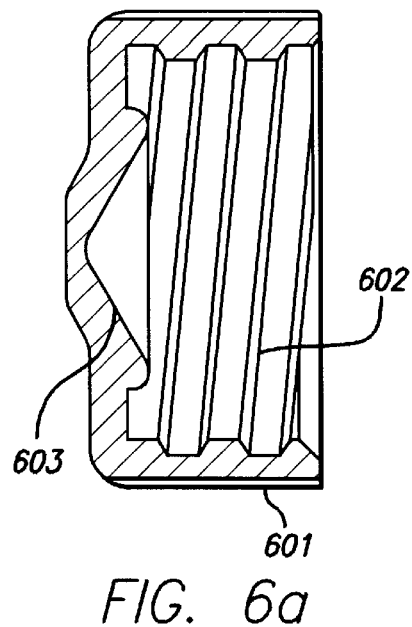
FIGS. 6a–d illustrate a cap in accordance with an embodiment of the instant invention.
Figure 6B:
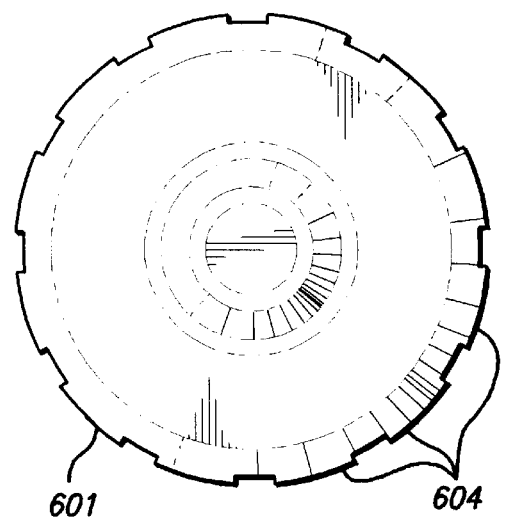
Figure 6C:
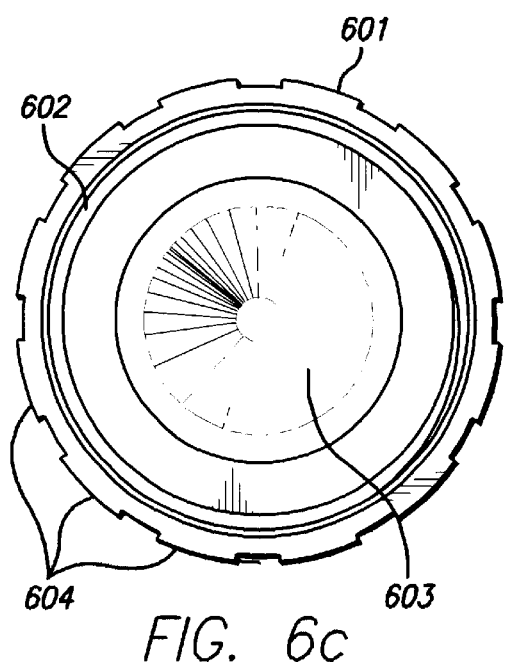
Figure 6D:
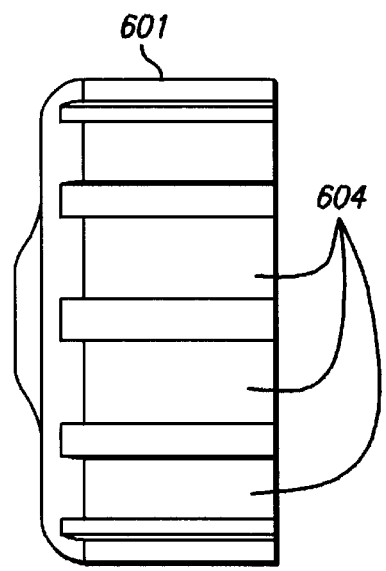

The injector attachment mechanism 501 may further include a center hole 503 (FIGS. 5a, 5b, and 5c) configured to receive a portion of the coupling device 101. The coupling device 101 may traverse the center hole 503, and, furthermore, at least a portion of the injector end 401 of the coupling device 101 may be larger in diameter than the center hole 503. In this configuration (FIGS. 3 and 8b), affixing the injector attachment mechanism 501 to the needle-less injector 102 may secure the coupling device 101 to the needle-less injector 102.

The injector attachment mechanism 501 may also include ridges 504 disposed about its exterior circumference. The ridges 504 may provide a user with additional support in gripping the injector attachment mechanism 501 when attaching it to or removing it from a needle-less injector 103.

Figure 9:
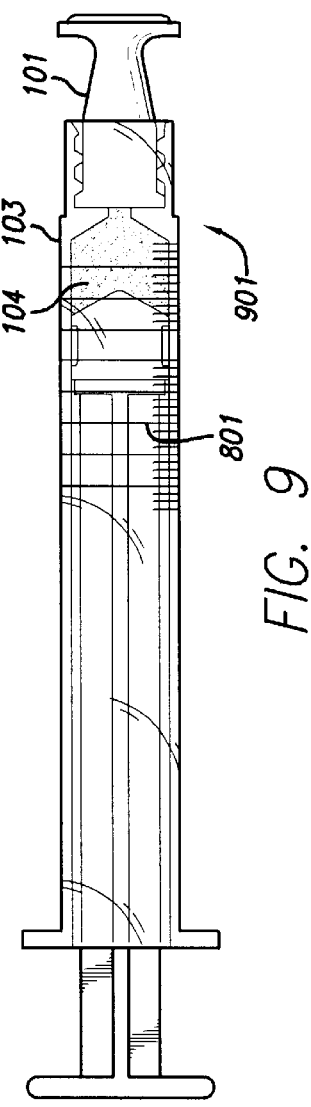
FIG. 9 illustrates a side perspective view of a filling device in accordance with an embodiment of the instant invention. The filling device includes a coupling device and a vessel.

As depicted in FIGS. 4a, 4b, and 4d, the vessel end 402 of the coupling device 101 may include a vessel attachment mechanism 406 that may serve to affix the coupling device 101 to a vessel 103 (FIGS. 1, 2, and 3). The coupling device 101 may be temporarily affixed to a vessel 103, or, in an alternate embodiment illustratively depicted in FIG. 9, the coupling device 101 may be affixed to a vessel 103, to create a filling device 901.

In one embodiment of the instant invention, a vessel attachment mechanism 406 may include two elevated tabs disposed opposite one another, and that further cooperate with a vessel attachment receiving mechanism 302 of a vessel 103 (FIG. 3). In the embodiment illustratively depicted in FIG. 3, a vessel attachment receiving mechanism 302 is embodied in an interior screw threading; although other attachment mechanisms 406 and vessel attachment receiving mechanisms 302 may be utilized. For example, various vessels 103 may include vessel attachment receiving mechanisms 302, such as snap fittings, pressure fittings, or the like. In such alternate embodiments, a corresponding vessel attachment mechanism 406 may be selected and configured accordingly.

In those embodiments wherein the vessel 103 is a Luer syringe, the coupling device 101 may be further adapted to receive the particular configuration of the Luer syringe. As depicted in FIGS. 4a and 4b, such adaptation may include a multiple-diameter channel 403. The coupling device 101 may include a channel 403 with a segment of large diameter 407, a segment of small diameter 408, and a conical segment 409 configured between the segment of small diameter 408 and the orifice 405. An angled shoulder 410 may also be included between the segment of large diameter 407 and the segment of small diameter 408. The angled shoulder 410 may correspond to an angle at the tip of a protruding tube 301; thereby enhancing the mating of the vessel 103 and the coupling device 101, when the two are attached (FIGS. 1, 2, and 3).

Upon attaching the coupling device 101 to the Luer syringe or other vessel 103, a protruding tube 301 of a Luer syringe or other vessel 103 may reside, at least partially, inside the segment of the channel 403 of large diameter 407.

In such embodiments, illustratively depicted in FIGS. 1, 2, and 3, fluid may flow from the protruding tube 301, through the segment of the channel 403 of small diameter 408, the conical segment 409, and the orifice 405 of the coupling device 101, then through the dispensing orifice 203 to fill a needle-less injector 102.

As depicted in FIG. 8, vessel graduations 801 may be included on the vessel 103. Similar injector graduations 802 may be included on the needle-less injector 102. Such graduations may provide a user with visual cues to aid in determining when a desirable amount of fluid 104 has been transferred between the vessel 103 and the needle-less injector 102. When making such determinations by observing vessel graduations 801, a user may need to account for the volume of fluid 104 that may remain within the channel 403 of the coupling device 101 after a filling operation is completed.

In an embodiment of the instant invention, the vessel includes filling equipment 1000 (FIG. 10) configured to fill at least one needle-less injector. The filling equipment 1000 may include a reservoir 1001 of fluid 104. The vessel end 402 of the coupling device 101 may be configured in a manner appropriate to provide fluid communication between the injector end of the coupling device 101 and the equipment 1000. In various embodiments, such as that depicted in FIG. 10a, the coupling device 101 may be attached to a conduit 1003, such as a hose or tube, that provides fluid communication between the coupling device 101 and the equipment 1000. An adapter 1002 may be included to connect the coupling device 101 to the conduit 1003. In an alternate embodiment, as depicted in FIG. 10b, multiple coupling devices 101 may be attached to a corresponding series of conduits 1003 which, in turn, connect to filling equipment 1000, thereby providing fluid communication between the filling equipment 1000 and the multiple coupling devices 101. Adapters 1002 may be included for each of the coupling devices 101 included therein.

Figure 7:
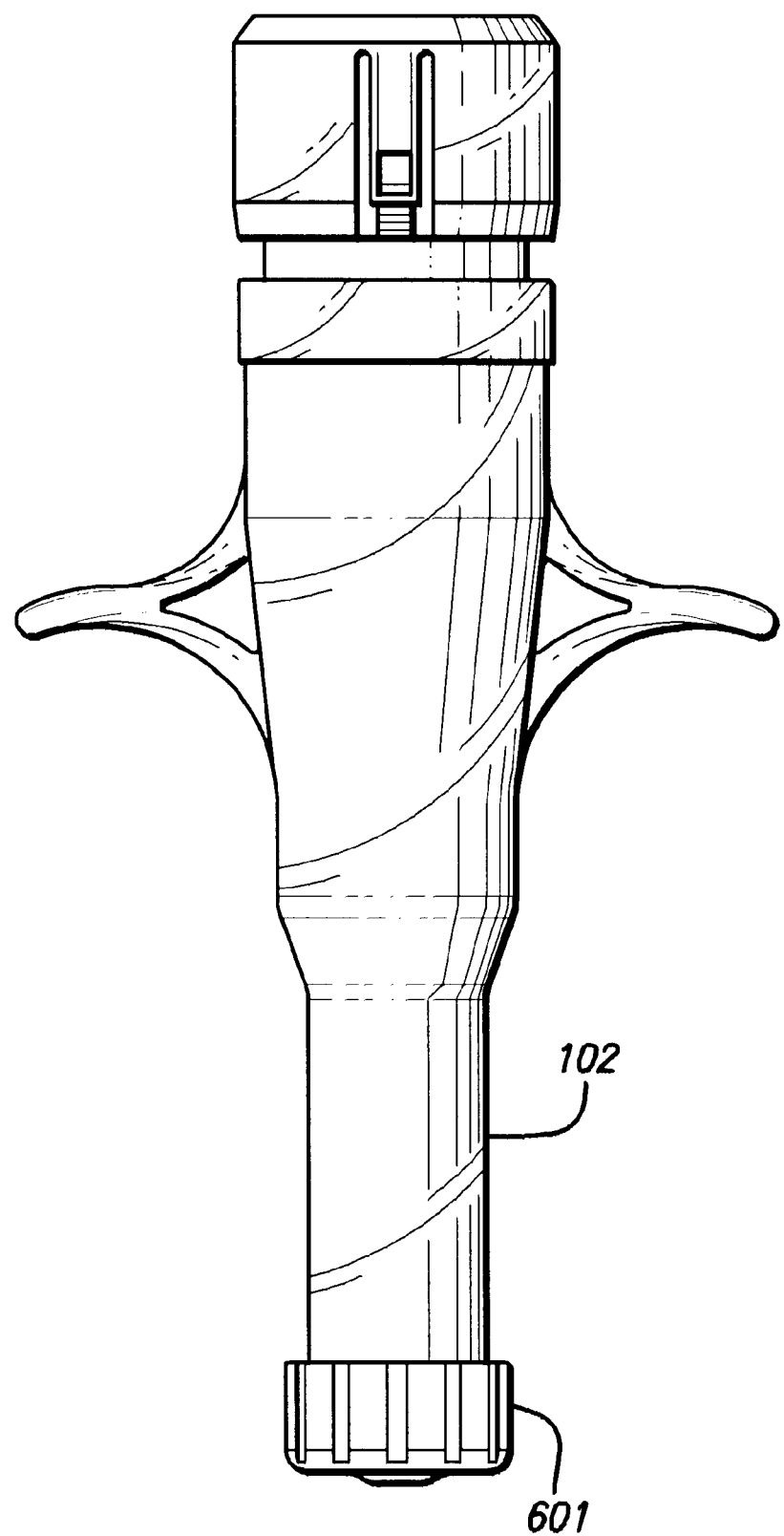
FIG. 7 illustrates a perspective view of a needle-less injector in accordance with an embodiment of the instant invention. A cap is included on the needle-less injector.

As depicted in FIGS. 6 and 7, an injector cap 601 may be included in an embodiment of the present invention to protect the receiving surface 204 of the dispensing end 202 of the needle-less injector 102 when the injector 102 is being neither filled or refilled nor used to administer a needle-less injection. The injector cap 601 may include a cap attachment mechanism 602 that cooperates with an injector attachment mechanism 205. In one embodiment, as depicted in FIG. 6, the cap attachment mechanism 602 is embodied in an interior screw threading, and the injector attachment mechanism 205 is embodied in an exterior screw threading. Other suitable cap attachment mechanisms 602 may be utilized, as well, such as snap fittings, pressure fittings, or the like.

The injector cap may also include an interior depression 603 configured to receive the receiving surface 204 of a needle-less injector 102. The injector cap 601 may also include grips 604 disposed about the exterior circumference. The grips 604 may provide a user with additional support in gripping the cap 601 when attaching it to or removing it from a needle-less injector 103.

Figure 12A:
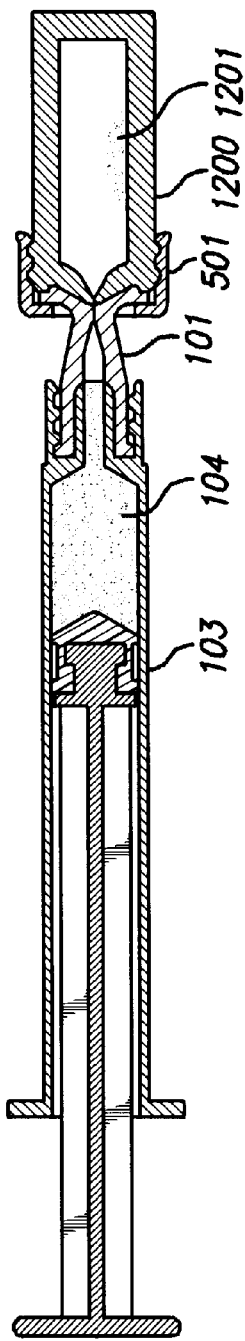
FIGS. 12a–d illustrate the preparation of a mixture in accordance with an embodiment of the present invention.
Figure 12B:
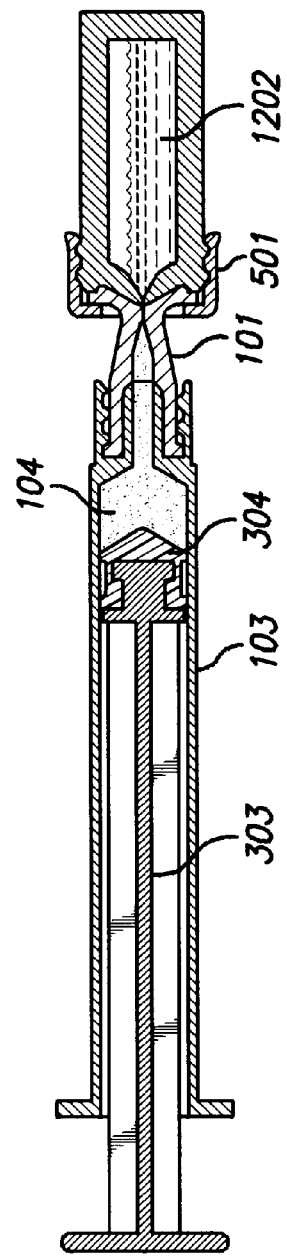
Figure 12C:
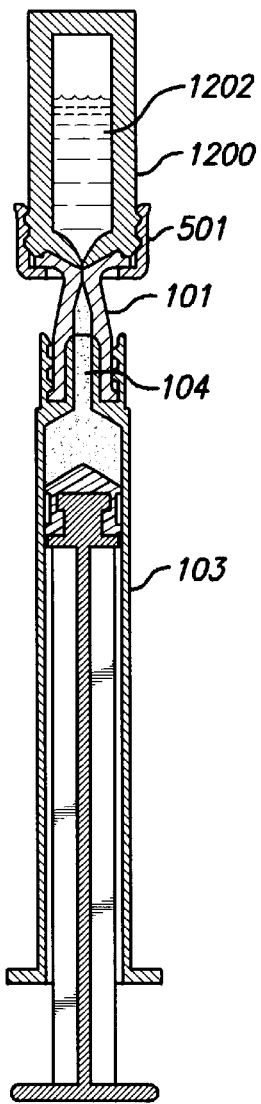
Figure 12D:
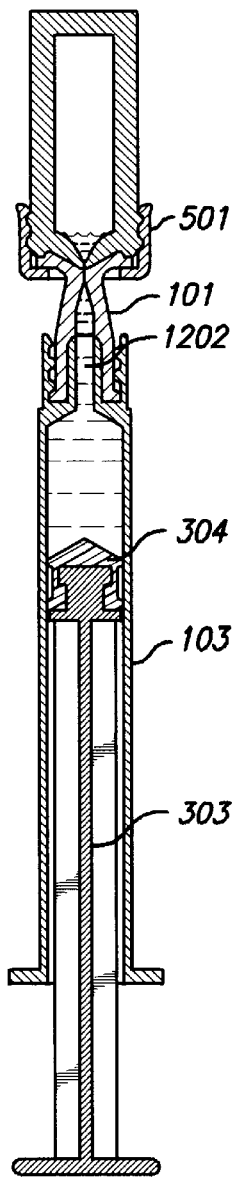
Figure 13:
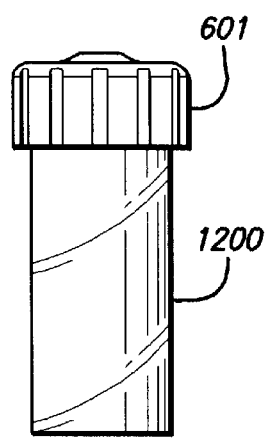
FIG. 13 illustrates a side perspective view of a storage vial with a cap in accordance with an embodiment of the present invention.

As depicted in FIGS. 12a–d, in an alternate embodiment of the present invention, a coupling device 101 may be mated or attached to a storage vial 1200 (FIG. 13). The storage vial 1200 may include a portion that is contoured such that, when it is attached or mated to a coupling device 101, a fluid or mixture that is transferred through the coupling device 101 does not contact the exterior surface of the storage vial 1200. The contoured portion of the storage vial 1200 may be similar to the contour of a receiving surface of a needle-less injector that is filled with a fluid or mixture withdrawn from the storage vial 1200. This configuration may avoid the deposit of a fluid or mixture that is transferred between the coupling device 101 and the storage vial 1200 on the exterior surface of either the coupling device 101 or the storage vial 1200.

The storage vial 1200 may further include a vial orifice that is similar to the dispensing orifice 203 included on the needle-less injector 102 (FIG. 11). The vial orifice may be larger, smaller, or similar in diameter to the orifice 405 configured on the coupling device 101 with which it may align when the coupling device 101 and the storage vial 1200 are either mated or attached to one another.

In the embodiment depicted in FIGS. 12a–d, the coupling device 101 includes an injector attachment mechanism 501 that communicates with exterior screw threading on the surface of the storage vial 1200. However, it will be readily recognized by one in the art that alternate means of attaching the storage vial 1200 to the coupling device 101 may be employed, such as a pressure fitting, a snap fitting, or the like. The coupling device may be simultaneously mated or attached with a vessel attachment mechanism to a vessel 103. Any suitable vessel 103 may be utilized, as described in any of the embodiments discussed herein.

In one embodiment of the present invention, the storage vial 1200 may contain a product 1201, and the vessel 103 may contain a fluid 104 (FIG. 12a). Fluid 104 may be transferred from the vessel 103 to the storage vial 1200 through the coupling device 101 (FIG. 12b). The fluid 104 and the product 1201 may mix in the storage vial 1200 to form a mixture 1202. It may be advantageous to further mix the fluid 104 and product 1202 by agitating the two components in the storage vial 1200 such as by shaking the assembly. The storage vial 1200 may then be oriented above the coupling device 101 (FIG. 12c) and the mixture 1202 may be drawn out of the storage vial 1200 (FIG. 12d). Notably, the storage vial 1200 need not be oriented above the vessel 103 to withdraw a fluid or mixture therefrom; however, this may avoid the transfer of air contained in the storage vial into the vessel 103. The storage vial 1200 may then be removed from the coupling device 101, and a needle-less injector 102 may then be filled with the mixture 1202 in accordance with any of the embodiment discussed herein.

To more fully blend the mixture 1202, in some embodiments and with certain products and fluids, it may be advantageous to shuttle the mixture 1202 between the vessel 103 and the storage vial 1200. In the embodiment depicted in FIGS. 12a–d (i.e., including a Luer syringe as the vessel 103), this may be accomplished by sequentially depressing and then pulling back on the plunger of the vessel 103. This process may be repeated to achieve a satisfactory blending of the components of the mixture 1202.

In an alternate embodiment of the present invention, the storage vial 1200 may contain a fluid (not shown). The fluid may be withdrawn from the storage vial 1200 in a manner similar to the withdrawal of the mixture 1202 depicted in FIGS. 12c and 12d (e.g., by orienting the storage vial 1200 above the coupling device 101 and withdrawing the contents of the storage vial 1200 through the coupling device 101 into the vessel 103). A vessel 103 may be void of any fluid or product prior to the withdrawal of fluid or mixture from a storage vial 1200. However, in alternate embodiments, the vessel 103 may initially contain a latent fluid, a lyophilized solid, a non-lyophilized solid, or any other suitable product. In these latter embodiments, a mixture may be created in the vessel 103 upon withdrawing a fluid from the storage vial 1200. Air may be expelled from the vessel 103 in any of the aforementioned embodiments by either expelling that air into the storage vial 1200 or, once the storage vial 1200 is separated from the coupling device 101, by expelling that air into the local atmosphere. In those embodiments of the present invention where the vessel 103 includes a plunger (FIGS. 12*a–d*), depressing the plunger may expel the air from the vessel 103, especially if the vessel 103 is oriented such that the plunger is below the coupling device 101.

A cap 601 may be included on the storage vial 1200 when the storage vial 1200 is neither mated nor attached to a coupling device 101 (FIG. 13). This cap 601 may be similar or even identical to the cap 601 that may be included on a needle-less injector 102 (FIG. 7) when it is being neither filled nor used to administer a needle-less injection.

EXAMPLE 1

Filling a Needle-Less Injector Using a Coupling Device

A Luer syringe containing a pharmaceutical fluid is affixed to the vessel end of a coupling device, by screwing the elements together (i.e., two elevated tabs on the vessel end of the coupling device cooperate with interior screw threading on the Luer syringe). The cap is removed from the dispensing end of a needle-less injector, and the injector is attached to the injector end of the coupling device, also by screwing the elements together (i.e., exterior screw threading disposed upon the needle-less injector cooperates with interior screw threading configured upon an injector attachment mechanism). The needle-less injector contains no fluid.

The plunger of the Luer syringe is depressed, forcing the pharmaceutical fluid out through a protruding tube on the Luer syringe, through a channel in the coupling device, through corresponding orifices disposed on the coupling device and needle-less injector, and into the needle-less injector. Graduations on the needle-less injector provide a user with a visual cue to determine when the desirable amount of fluid has been introduced into the same. Upon filling the needle-less injector with the desirable amount of pharmaceutical fluid, if necessary, the user pulls back on the plunger of the Luer syringe, evacuating air bubbles from the needle-less injector. The needle-less injector and vessel are then separated from the coupling device, by unscrewing all three elements.

EXAMPLE 2

Filling a Needle-Less Injector Using a Filling Device

A filling device includes both a vessel and a coupling device. The filling device is mated to a needle-less injector by holding the injector end of the coupling device against the receiving surface on a dispensing end of a needle-less injector. The vessel included in the filling device is a syringe, affixed to the coupling device with a snap fitting. The needle-less injector contains a lyophilized solid medication prior to filling via the coupling device, and the filling device contains a diluent.

The plunger of the filling device is depressed, forcing the diluent through the coupling device, through corresponding orifices disposed on the coupling device and needle-less injector, and into the needle-less injector. Graduations on the Luer syringe provide a user with a visual cue to determine when the desirable amount of diluent has been introduced into the injector. Upon filling the needle-less injector with the desirable amount of diluent, if necessary, the user pulls back on the plunger of the filling device, evacuating air bubbles from the needle-less injector. The needle-less injector and filling device are then separated from one another.

EXAMPLE 3

Filling a Needle-Less Injector Using Filling Equipment

Filling equipment includes a reservoir of a pharmaceutical fluid and a series of tubes, each of which terminates with an adapter. A vessel end of a coupling device is connected to each of the adapters. A series of needle-less injectors is mated to the series of coupling devices, and an amount of the pharmaceutical fluid is filled into each needle-less injector.

After each of the needle-less injectors is filled with an amount of the pharmaceutical fluid, the coupling devices are removed from the needle-less injectors and another series of needle-less injectors is mated to the same coupling devices. An amount of the pharmaceutical fluid is then filled into each of this second series of needle-less injectors.

After each of the second series of needle-less injectors has been filled with an amount of the pharmaceutical fluid, the coupling devices are removed from the needle-less injectors, and a rubber cap is placed on each.

EXAMPLE 4

Preparing a Vessel for Filling a Needle-Less Injector with a Fluid Using a Coupling Device and a Storage Vial A Luer syringe is affixed to the vessel end of a coupling device, by screwing the, elements together (i.e., two elevated tabs on the vessel end of the coupling device cooperate with interior screw threading on the Luer syringe). The cap is removed from a storage vial, and the storage vial is attached to the injector end of the coupling device, also by screwing the elements together (i.e., exterior screw threading disposed upon the storage vial cooperates with interior screw threading configured upon an attachment mechanism). The storage vial contains a fluid.

The storage vial is oriented above the Luer syringe to minimize transfer of air therefrom. The plunger of the Luer syringe is then pulled back, withdrawing the fluid out of the storage vial through corresponding orifices disposed on the storage vial and coupling device, through a channel in the coupling device, through a protruding tube on the Luer syringe, and into the Luer syringe. Graduations on the Luer syringe provide a user with a visual cue to determine when the desirable amount of fluid has been withdrawn into the same. Upon filling the Luer syringe with the desirable amount of fluid, if necessary, the user depresses the plunger of the Luer syringe, evacuating air bubbles from the Luer syringe. The storage vial and coupling device are then separated from one another, by unscrewing the two elements. The Luer syringe and coupling device may then be used to fill a needle-less injector with the fluid.

EXAMPLE 5

Preparing a Vessel for Filling a Needle-Less Injector with a Mixture Using a Coupling Device and a Storage Vial A Luer syringe is affixed to the vessel end of a coupling device, by screwing the elements together (i.e., two elevated tabs on the vessel end of the coupling device cooperate with interior screw threading on the Luer syringe). The cap is removed from a storage vial, and the storage vial is attached to the injector end of the coupling device, also by screwing the elements together (i.e., exterior screw threading disposed upon the storage vial cooperates with interior screw threading configured upon an attachment mechanism). The storage vial contains a lyophilized solid product and the Luer syringe contains a solvent.

The plunger of the Luer syringe is then depressed, forcing the solvent out through a protruding tube on the Luer syringe, through a channel in the coupling device, through corresponding orifices disposed on the coupling device and storage vial, and into the storage vial. Graduations on the Luer syringe provide a user with a visual cue to determine when the desirable amount of solvent has been dispensed from the same. The solvent mixes with the lyophilized solid product in the storage vial. Where necessary, the entire assembly is shaken to more fully blend the mixture of the lyophilized solid product and the solvent and/or the mixture is shuttled back and forth between the storage vial and Luer syringe to more fully blend the mixture.

The storage vial is then oriented above the Luer syringe to minimize transfer of air therefrom. The plunger of the Luer syringe is then pulled back, withdrawing the mixture out of the storage vial through corresponding orifices disposed on the storage vial and coupling device, through a channel in the coupling device, through a protruding tube on the Luer syringe, and into the Luer syringe. Graduations on the Luer syringe provide a user with a visual cue to determine when the desirable amount of the mixture has been withdrawn into the same. Upon filling the Luer syringe with the desirable amount of the mixture, if necessary, the user depresses the plunger of the Luer syringe, evacuating air bubbles from the Luer syringe. The storage vial and coupling device are then separated from one another, by unscrewing the two elements. The Luer syringe and coupling device may then be used to fill a needle-less injector with the mixture.

While the description above refers to particular embodiments of the present invention, it should be readily apparent to people of ordinary skill in the art that a number of modifications may be made without departing from the spirit thereof The accompanying claims are intended to cover such modifications as would fall within the true spirit and scope of the invention. The presently disclosed embodiments are, therefore, to be considered in all respects as illustrative and not restrictive, the scope of the invention being indicated by the appended claims rather than the foregoing description. All changes that come within the meaning of and range of equivalency of the claims are intended to be embraced therein.

What is claimed is:

1. A coupling device to fill a needle-less injector comprising:
   a contact surface configured to mate non-frangibly with a receiving surface of a needle-less injector;
   an orifice disposed upon said contact surface;
   a vessel end configured to affix said coupling device to a vessel; and
   an unobstructed channel to provide fluid communication between said orifice and said vessel end,
   wherein said coupling device is asymmetrical across a plane perpendicular to an axis of said unobstructed channel.

2. The coupling device of claim 1, further comprising an injector attachment mechanism to attach said coupling device to said needle-less injector.

3. The coupling device of claim 2, wherein said injector attachment mechanism further includes an attachment fitting selected from the group consisting of a screw threading, a snap fitting, and a pressure fitting.

4. The coupling device of claim 2, wherein said injector attachment mechanism includes a screw threading.

5. The coupling device of claim 2, wherein said injector attachment mechanism further includes grips.

6. The coupling device of claim 1, wherein said vessel is a Luer syringe.

7. The coupling device of claim 1, further comprising a vessel attachment mechanism to attach said coupling device to a vessel.

8. The coupling device of claim 7, wherein said vessel attachment mechanism is selected from the group consisting of at least one elevated tab, a screw threading, a snap fitting, and a pressure fitting.

9. The coupling device of claim 8, further including a vessel attachment receiving mechanism.

10. The coupling device of claim 9, wherein said vessel is a Luer syringe, said vessel attachment mechanism is two elevated tabs, and said vessel attachment receiving mechanism is an interior screw threading that cooperates with said two elevated tabs.

11. The coupling device of claim 1, wherein said channel further includes a cylindrical segment.

12. The coupling device of claim 11, wherein said channel further includes a conical segment disposed between said cylindrical segment and said orifice.

13. The coupling device of claim 1, wherein said orifice includes a diameter smaller than a diameter of a dispensing orifice disposed upon said receiving surface.

14. The coupling device of claim 1, wherein said vessel is filling equipment.

15. The coupling device of claim 14, wherein said filling equipment further includes a reservoir configured to contain a fluid.

16. The coupling device of claim 14, wherein said filling equipment further includes a conduit to provide fluid communication between said coupling device and said filling equipment.

17. The coupling device of claim 16, wherein said filling equipment further includes an adapter to connect said conduit to said coupling device.

18. The coupling device of claim 14, wherein said filling equipment is configured to fill multiple needle-less injectors.

19. The coupling device of claim 14, wherein said coupling device is configured to be sequentially mated to a series of needle-less injectors.

20. The coupling device of claim 14, further including at least two coupling devices.

21. The coupling device of claim 20, wherein said at least two coupling devices are configured to be simultaneously mated to a group of needle-less injectors.

22. The coupling device of claim 21, wherein said at least two coupling devices are configured to be sequentially mated to a series of said groups of needle-less injectors.

23. A coupling device to fill a needle-less injector comprising:
   a contact surface configured to mate with a receiving surface of a needle-less injector;
   an orifice disposed upon said contact surface;
   a vessel end configured to affix said coupling device to a vessel; and
   a channel to provide fluid communication between said orifice and said vessel end,
   wherein said channel further includes a cylindrical segment, wherein said channel further includes a conical segment disposed between said cylindrical segment and said orifice, and wherein said cylindrical segment is configured to matingly receive a Luer syringe.

24. The coupling device of claim 23, wherein said cylindrical segment further includes:
   a segment of large diameter; and
   a segment of small diameter configured between said segment of large diameter and said conical segment.

25. The coupling device of claim 24, wherein said cylindrical segment further includes a shoulder configured between said segment of large diameter and said segment of small diameter, said shoulder being configured at an angle similar to an angle of a tip of a protruding tube of said Luer syringe.

26. A coupling device to fill a needle-less injector comprising:
   a contact surface configured to mate with a receiving surface of a needle-less injector;
   an orifice disposed upon said contact surface;
   a vessel end configured to affix said coupling device to a vessel;
   a channel to provide fluid communication between said orifice and said vessel end; and
   an injector attachment mechanism to attach said coupling device to said needle-less injector,
   wherein said injector attachment mechanism is configured to attach said coupling device to a storage vial.

27. A filling device to fill a needle-less injector comprising:
   a vessel to contain a fluid and including a protruding tube; and
   a coupling device including:
      a contact surface configured to mate non-frangibly with a receiving surface of a needle-less injector;
      an orifice disposed upon said contact surface; and
      a channel to provide fluid communication between said orifice and said vessel, said protruding tube residing at least partially within said channel,
   wherein said filling device is asymmetrical across a plane perpendicular to an axis of said channel.

28. The filling device of claim 27, further comprising an injector attachment mechanism to attach said filling device to said needle-less injector.

29. The filling device of claim 28, wherein said injector attachment mechanism further includes an attachment fitting selected from the group consisting of a screw threading, a snap fitting, and a pressure fitting.

30. The filling device of claim 28, wherein said injector attachment mechanism includes a screw threading.

31. The filling device of claim 28, wherein said injector attachment mechanism further includes grips.

32. The filling device of claim 27, wherein said vessel is a Luer syringe.

33. The filling device of claim 27, further comprising a vessel attachment mechanism to attach said coupling device to said vessel.

34. The filling device of claim 33, wherein said vessel attachment mechanism is selected from the group consisting of at least one elevated tab, a screw threading, a snap fitting, and a pressure fitting.

35. The filling device of claim 34, further including a vessel attachment receiving mechanism.

36. The filling device of claim 35, wherein said vessel is a Luer syringe, said vessel attachment mechanism is two elevated tabs, and said vessel attachment receiving mechanism is an interior screw threading that cooperates with said two elevated tabs.

37. The filling device of claim 27, wherein said channel further includes a cylindrical segment.

38. The filling device of claim 37, wherein said channel further includes a conical segment disposed between said cylindrical segment and said orifice.

39. A filling device to fill a needle-less injector comprising:
   a vessel to contain a fluid and including a protruding tube; and
   a coupling device including:
      a contact surface configured to mate with a receiving surface of a needle-less injector;
      an orifice disposed upon said contact surface; and
      a channel to provide fluid communication between said orifice and said vessel, said protruding tube residing at least partially within said channel,
   wherein said channel further includes a cylindrical segment,
   wherein said channel further includes a conical segment disposed between said cylindrical segment and said orifice, and
   wherein said cylindrical segment is configured to matingly receive a Luer syringe.

40. The filling device of claim 39, wherein said cylindrical segment further includes:
   a segment of large diameter; and
   a segment of small diameter configured between said segment of large diameter and said conical segment.

41. The filling device of claim 40, wherein said cylindrical segment further includes a shoulder configured between segment of large diameter and said segment of small diameter, said shoulder being configured at an angle similar to an angle of a tip of a protruding tube of said Luer syringe.

42. A filling device to fill a needle-less injector comprising:
   a vessel to contain a fluid and including a protruding tube; and
   a coupling device including:
      a contact surface configured to mate with a receiving surface of a needle-less injector;
      an orifice disposed upon said contact surface; and
      a channel to provide fluid communication between said orifice and said vessel, said protruding tube residing at least partially within said channel,
   wherein said orifice includes a diameter smaller than a diameter of a dispensing orifice disposed upon said receiving surface.

43. A filling device to fill a needle-less injector comprising:
   a vessel to contain a fluid and including a protruding tube; and
   a coupling device including:
      a contact surface configured to mate with a receiving surface of a needle-less injector;
      an orifice disposed upon said contact surface;
      a channel to provide fluid communication between said orifice and said vessel, said protruding tube residing at least partially within said channel; and
      an injector attachment mechanism to attach said filling device to said needle-less injector,
   wherein said injector attachment mechanism is configured to attach said filling device to a storage vial.

44. In combination, a needle-less injector and a coupling device configured to fill said needle-less injector, said combination comprising:

said needle-less injector; and said coupling device, said coupling device being mated non-frangibly to said needle-less injector, and further including:
- a contact surface configured to mate with a receiving surface of said needle-less injector;
- an orifice disposed upon said contact surface;
- a vessel end configured to affix said coupling device to a vessel; and
- an unobstructed channel to provide fluid communication between said orifice and said vessel end.

45. The combination of claim 44, further comprising an injector attachment mechanism to attach said coupling device to said needle-less injector.

46. The combination of claim 45, wherein said injector attachment mechanism further includes an attachment fitting selected from the group consisting of a screw threading, a snap fitting, and a pressure fitting.

47. The combination of claim 45, wherein said attachment mechanism includes a screw threading.

48. The combination of claim 45, wherein said injector attachment mechanism further includes grips.

49. The combination of claim 44, wherein said vessel is a Luer syringe.

50. The combination of claim 44, further comprising a vessel attachment mechanism configured to attach said coupling device to a vessel.

51. The combination of claim 50, wherein said vessel attachment mechanism is selected from the group consisting of at least one elevated tab, a screw threading, a snap fitting, and a pressure fitting.

52. The combination of claim 51, wherein said vessel attachment mechanism is two elevated tabs.

53. The combination of claim 45, wherein said channel further includes a cylindrical segment.

54. The combination of claim 53, wherein said channel further includes a conical segment disposed between said cylindrical segment and said orifice.

55. The combination of claim 54, wherein said cylindrical segment further includes:
- a segment of large diameter; and
- a segment of small diameter configured between said segment of large diameter and said conical segment.

56. The combination of claim 55, wherein said cylindrical segment further includes a shoulder configured between said segment of large diameter and said segment of small diameter, said shoulder being configured at an angle similar to an angle of a tip of a protruding tube of said Luer syringe.

57. The combination of claim 44, wherein said orifice includes a diameter smaller than a diameter of a dispensing orifice disposed upon said receiving surface.

58. The combination of claim 44, wherein said vessel is filling equipment.

59. In combination, a needle-less injector and a coupling device configured to fill said needle-less injector, said combination comprising:

said needle-less injector; and said coupling device, said coupling device being mated to said needle-less injector, and further including:
- a contact surface configured to mate with a receiving surface of said needle-less injector;
- an orifice disposed upon said contact surface;
- a vessel end configured to affix said coupling device to a vessel;
- a channel to provide fluid communication between said orifice and said vessel end; and
- an injector attachment mechanism to attach said coupling device to said needle-less injector,
- wherein said channel further includes a cylindrical segment,
- wherein said channel further includes a conical segment disposed between said cylindrical segment and said orifice, and
- wherein said cylindrical segment is configured to matingly receive a Luer syringe.

60. A method of filling a needle-less injector, said method comprising:

providing a coupling device comprising:
- a contact surface configured to mate non-frangibly with a receiving surface of a needle-less injector,
- an orifice disposed upon said contact surface,
- a vessel end configured to affix said coupling device to a vessel, and
- an unobstructed channel to provide fluid communication between said orifice and said vessel end,
- wherein said coupling device is asymmetrical across a plane perpendicular to an axis of said unobstructed channel;

mating said coupling device at said vessel end to a vessel;

mating said coupling device at said contact surface to a needle-less injector, to provide fluid communication between said needle-less injector and said vessel; and dispensing a volume of fluid from said vessel to said needle-less injector.

61. The method of claim 60, wherein mating said vessel to said coupling device comprises screwing said vessel and said coupling device together.

62. The method of claim 60, wherein mating said needle-less injector to said coupling device comprises holding said contact surface against a receiving surface disposed upon said needle-less injector.

63. The method of claim 60, wherein mating said needle-less injector to said coupling device comprises attaching said needle-less injector to said coupling device.

64. The method of claim 63, wherein attaching said needle-less injector to said coupling device comprises screwing said needle-less injector and an injector attachment mechanism configured upon said coupling device together.

65. The method of claim 60, wherein said needle-less injector is void of fluid prior to dispensing said volume of said fluid from said vessel.

66. The method of claim 60, wherein said needle-less injector is at least partially filled with a latent fluid, a lyophilized solid, a non-lyophilized solid, or another product prior to dispensing said volume of said fluid from said vessel.

67. The method of claim 60, wherein dispensing said volume of said fluid from said vessel comprises depressing a plunger operably attached to said vessel.

68. The method of claim 60, further including removing air from said needle-less injector.

69. The method of claim 68, wherein removing said air comprises pulling back on a plunger operably attached to said vessel.

70. The method of claim 60, further including measuring said volume of said fluid dispensed from said vessel into said needle-less injector by comparing a level of said fluid in said vessel with graduations disposed upon said vessel.

71. The method of claim 60, further including removing a cap from said needle-less injector prior to mating said coupling device to said needle-less injector.

72. The method of claim 60, wherein said vessel is filling equipment.

73. The method of claim 60, further including separating said coupling device from said vessel and said needle-less injector after dispensing said volume of said fluid from said vessel.

74. The method of claim 73, wherein separating said vessel from said coupling device further includes unscrewing said vessel from said coupling device.

75. The method of claim 73, further including screwing a cap onto said needle-less injector after separating said coupling device from said needle-less injector.

76. The method of claim 60, wherein prior to mating said coupling device at said second end thereof to said needle-less injector, said method further includes:
mating said coupling device at said second end thereof to a storage vial, to provide fluid communication between said storage vial and said vessel;
withdrawing a volume of fluid from said storage vial to said vessel; and
separating said coupling device from said storage vial.

77. The method of claim 76, wherein mating said coupling device to said storage vial comprises attaching said coupling device to said storage vial.

78. The method of claim 77, wherein attaching said coupling device to said storage vial comprises screwing said storage vial and an attachment mechanism configured upon said coupling device together.

79. The method of claim 76, wherein said vessel is void of fluid prior to withdrawing said volume of said fluid from said storage vial to said vessel.

80. The method of claim 76, wherein said vessel is at least partially filled with a latent fluid, a lyophilized solid, a non-lyophilized solid, or another product prior to withdrawing said volume of said fluid from said storage vial to said vessel.

81. The method of claim 76, wherein withdrawing said volume of said fluid from said storage vial to said vessel comprises pulling back on a plunger operably attached to said vessel.

82. The method of claim 76, wherein prior to withdrawing said volume of fluid from said storage vial to said vessel, said method further includes:
dispensing a volume of fluid from said vessel to said storage vial; and
mixing said volume of fluid with a product contained in said storage vial to create a mixture.

83. The method of claim 82, wherein withdrawing said volume of said fluid from said storage vial to said vessel comprises withdrawing a volume of said mixture from said storage vial to said vessel, and dispensing said volume of said fluid from said vessel to said needle-less injector comprises dispensing a volume of said mixture from said vessel to said needle-less injector.

84. The method of claim 82, wherein mixing said volume of said fluid with said product contained in said storage vial to create said mixture comprises agitating said storage vial.

85. The method of claim 82, further including shuffling said mixture between said vessel and said storage vial to blend said mixture.

86. The method of claim 76, further including removing a cap from said storage vial prior to mating said storage vial to said coupling device.

87. In combination, a storage vial and a coupling device configured to transfer a fluid, a mixture, or both between said storage vial and a vessel, said combination comprising:
said storage vial; and
said coupling device, said coupling device being mated to said storage vial, and further including:
a contact surface configured to mate with an exterior of said storage vial, and also configured to mate non-frangibly with a receiving surface of a needle-less injector,
an orifice disposed upon said contact surface,
a vessel end configured to affix said coupling device to a vessel, and
an unobstructed channel to provide fluid communication between said orifice and said vessel end,
wherein said coupling device is asymmetrical across a plane perpendicular to an axis of said unobstructed channel.

88. The combination of claim 87, further comprising an attachment mechanism to attach said coupling device to said storage vial.

89. The combination of claim 88, wherein said attachment mechanism further includes an attachment fitting selected from the group consisting of a screw threading, a snap fitting, and a pressure fitting.

90. The combination of claim 88, wherein said attachment mechanism includes a screw threading.

91. The combination of claim 90, wherein said attachment mechanism further includes grips.

92. The combination of claim 87, wherein said channel further includes a cylindrical segment.

93. The combination of claim 92, wherein said channel further includes a conical segment disposed between said cylindrical segment and said orifice.

94. The combination of claim 87, wherein said vessel is filling equipment.

* * * * *